United States Patent

Takagi

[11] 4,327,711
[45] May 4, 1982

[54] FLEXIBLE TUBE FOR AN ENDOSCOPE

[75] Inventor: Takeji Takagi, Machida, Japan

[73] Assignee: Olympus Optical Co., Ltd., Japan

[21] Appl. No.: 200,480

[22] Filed: Oct. 24, 1980

[30] Foreign Application Priority Data

Nov. 16, 1979 [JP] Japan .................. 54/148475

[51] Int. Cl.³ .............................. A61B 1/00
[52] U.S. Cl. ................... 128/4; 128/303.15
[58] Field of Search ..................... 128/4–9, 128/348, 349, 303.15

[56] References Cited

U.S. PATENT DOCUMENTS

| | | | |
|---|---|---|---|
| 2,424,064 | 7/1947 | Stegeman | 128/6 |
| 2,544,914 | 3/1951 | Cameron | 128/4 |
| 3,799,151 | 3/1974 | Fukaumi et al. | 128/4 |
| 3,948,251 | 4/1976 | Hosono | 128/4 |
| 3,960,143 | 6/1976 | Terada | 128/4 |
| 3,998,216 | 12/1976 | Hosono | 128/6 |
| 4,176,662 | 12/1979 | Frazer | 128/6 |

Primary Examiner—Robert W. Michell
Assistant Examiner—Angela D. Sykes
Attorney, Agent, or Firm—Ostrolenk, Faber, Gerb & Soffen

[57] ABSTRACT

In a flexible tube for an endoscope including a metallic braided texture and a sheath tube covering the braided texture, both of which form a bendable portion and/or a flexible portion of an endoscope through which bundles of optical fibres, a flexure controlling wire or the like are passed, the internal peripheral surface of the sheath tube which covers the metallic braided texture is formed with grooves which retain an antifriction agent therein.

7 Claims, 8 Drawing Figures

FLEXIBLE TUBE FOR AN ENDOSCOPE

BACKGROUND OF THE INVENTION

The invention relates to a flexible tube for an endoscope, and more particularly, to an improved flexible tube for an endoscope having antifriction agent distributed between a metallic braided texture and a sheath tube.

A conventional flexible endoscope which is used in the medical field is constructed as illustrated in FIG. 1. Specifically, it includes an operating end 2 which permits a variety of operations to be performed at the proximate end of the endoscope, and a flexible portion 3 of an increased length which is adapted to be inserted into a coeliac cavity of the patient. The operating end 2 is provided with an observation eyepiece assembly 4, a flexure controlling knob 5, an inlet opening 6 through which a treatment instrument such as forceps to treat an affected part is inserted, an instrument riser controlling knob 7, an air ventilation/water feed button 8, a suction button 9 and the like. The operating end is adapted to be connected to a light guide cord 10 which is in turn connected to an illumination light source, not shown. The flexible portion 3 which is adapted to be inserted into a coeliac cavity comprises an elongated freely flexible portion 11, a bendable portion 12 connected in contiguous relationship with the portion 11 to permit a distal end 13 to be directed in any desired orientation in response to an operation of the flexure controlling knob 5, and the distal end 13 contiguous with the bendable portion 12 and which is formed with an aillumination window, an observation window, an outlet opening to permit an access of the treatment instrument into or out of the distal end, air port/water port, all of which are not shown, A number of internal members pass through the flexible portion 11 and the bendable portion 12, including bundles of optical fibres serving as an image guide and a light guide, a tube for containing the treatment instrument therein, air/water supply channel, a wire for operating an instrument riser and the flexure controlling wire and the like. The distal end of these internal members are fixed within the distal end 13.

The bendable portion 12 which forms part of the portion 3 may be by way of example constructed as illustrated in FIG. 2. Specifically, portion 12 comprises a bendable tube 21 in the form of bellows which is formed by a series of articulated metal sleeves of a lesser individual length than portion 12, a metallic braided sheath 23 formed by a meshwork of thin metal wires braided into an annular configuration and applied over the bendable tube 21 so as to surround it, and a sheath tube 22 formed of a material such as rubber or synthetic resin and which is applied over the metallic braided sheath 23. The flexible portion 11 which represents the majority of the portion 3 comprises a helical flex. (see FIG. 7) formed by a helical winding of a band-shaped resilient blade, a metallic braided texture 33 (see FIG. 7) which is formed by a meshwork of thin metal wires braided into an annular configuration, and a sheath tube 32 formed of a material such as rubber or synthetic resin and applied over the braided sheath 33.

An antifriction agent comprising powder of molybdenum disulfide, boron nitride, a talc or the like is distributed between the metallic braided sheath 23 of the bendable portion 12 and its sheath tube 22 as well as between the metallic braided sheath 33 of the flexible portion 11 and its sheath tube 32, by applying it to the outer peripheral surface of the braided sheaths 23, 33 and to the inner peripheral surface of the sheath tubes 22, 32. Such antifriction agents are effective in reducing the degree of friction occurring between the metallic braided sheaths 23, 33 and the sheath tubes 22, 32 when the bendable portion 12 and the flexible portion 11 are flexed, and in preventing damage to the sheath tubes 22, 32 due to abrasion or an increase in the magnitude of force required to flex the bendable portion through the flexure controlling wire 25.

In the conventional construction of the bendable portion 12 and the flexible portion 11, the internal peripheral surface of the sheath tubes 22, 32 is smooth, so that the antifriction agent applied to and distributed between the braided sheaths 23, 33 and the sheath tubes 22, 32 may be scraped off from time to time during the use of the endoscope over a prolonged period of use. Such agent then finds its way into the bending tube 21 and the flex 31 through the meshes of the braided sheath 23, 33 and ultimately fall into the hollow interior of the tube 21 and the flex 31, thus greatly reducing the antifriction effect. This disadvantageously gives rise to a damage of the sheath tubes 22, 32 as a result of the abrasion of the internal surfaces, an increase in the magnitude of force required in operating the bendable and the flexible portion, or a breakage of the flexure controlling wire 25.

SUMMARY OF THE INVENTION

It is an object of the invention to eliminate above disadvantages of the prior art by providing a flexible tube for an endoscope in which the internal peripheral surface of sheath tubes which are located opposite to metallic braided textures is formed with grooves which retain an antifriction agent therein.

In accordance with the invention, the antifriction agent is applied to and retained in the grooves which are formed in the internal peripheral surface of a sheath tube, so that a reduction in the antifriction effect cannot be reduced over a prolonged period of use of the endoscope, thus preventing a damage to the sheath tube, an increase in the magnitude of force required to operate the bendable and the flexible portion, and a breakage of the flexure controlling wire.

DESCRIPTION OF PREFERRED EMBODIMENTS

Figure 1:
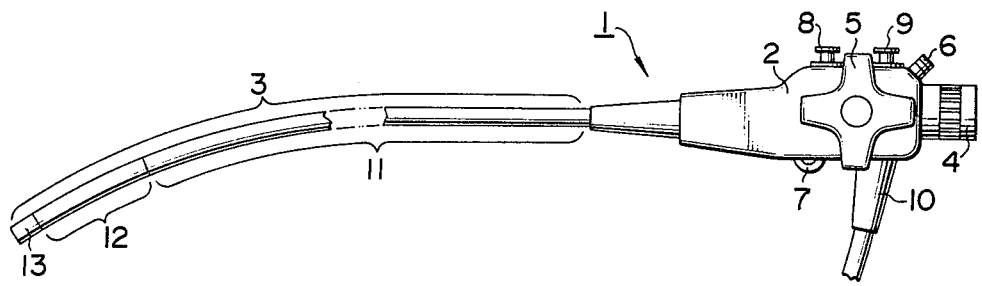
FIG. 1 is a front view of one form of a flexible endoscope.
Figure 2:
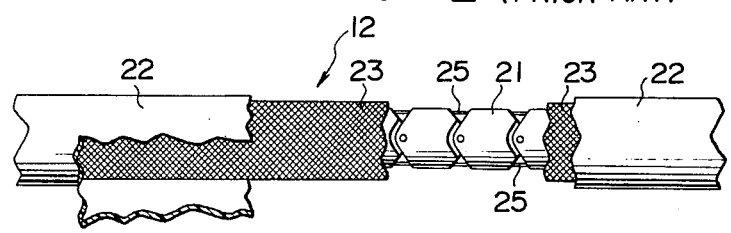
FIG. 2 is a plan view, partly cut away, of a bendable portion of a conventional flexible tube for an endoscope.
Figure 3:
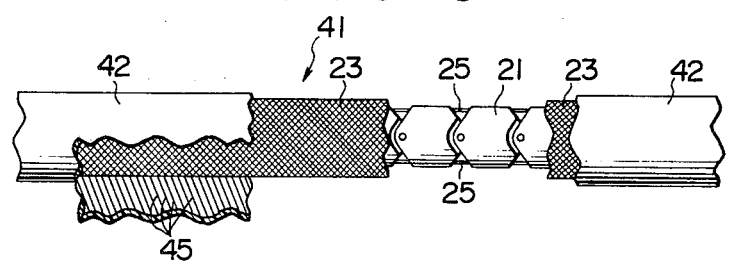
FIG. 3 is a plan view, partly cut away, of a bendable portion of a flexible tube for an endoscope which is constructed according to one embodiment of the invention.

Referring now to FIG. 3, there is shown a bendable portion of a flexible tube for an endoscope according to one embodiment of the invention. The bendable portion 41 of this embodiment differs from the bendable portion 12 of the prior art shown in FIG. 2 only in that an internal peripheral surface of a sheath tube 42 thereof is formed with narrow grooves 45 for retaining an antifriction agent therein and which extend in a helical manner with respect to the axis thereof. Hence, corresponding parts are designated by like reference characters as before, and will not be described. The grooves 45 may have a depth and a width, both of which may be any value not less than 0.01 mm. With this bendable portion 41, the antifriction agent is retained in the grooves 45, thus effectively preventing any reduction in the smoothness of movement which may be caused when the antifriction agent is scraped off.

Figure 4:
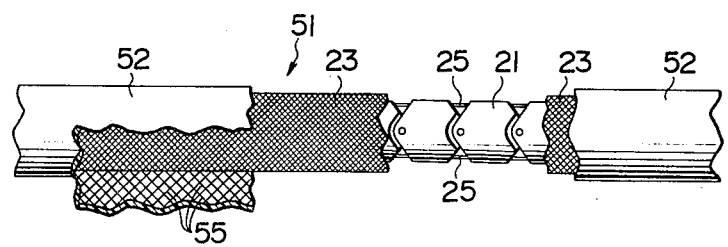
FIGS. 4 and 5 are similar plan views of flexible tubes for an endoscope according to other embodiments of the invention.
Figure 5:
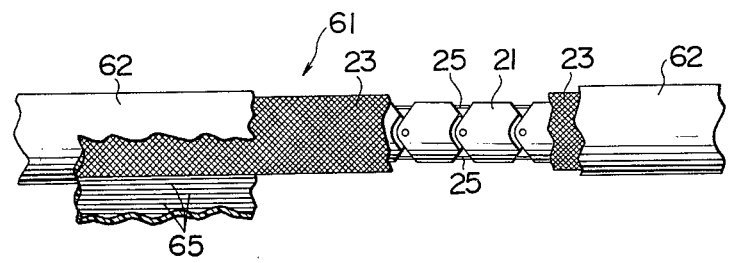

FIGS. 4 and 5 show other embodiments of the invention. Specifically, bendable portions 51, 61 which are used as part of the flexible tube for endoscope include sheath tubes 52, 62, respectively, the internal peripheral surface of which are formed with grooves 55 in the form of fine meshes and in the form of a number of axially extending narrow grooves 65, respectively. The formation of such grooves 55, 65 in the bendable portions 51, 61 achieves the same function and effect as those achieved with the bendable portion 41 shown in FIG. 3.

Figure 6A:
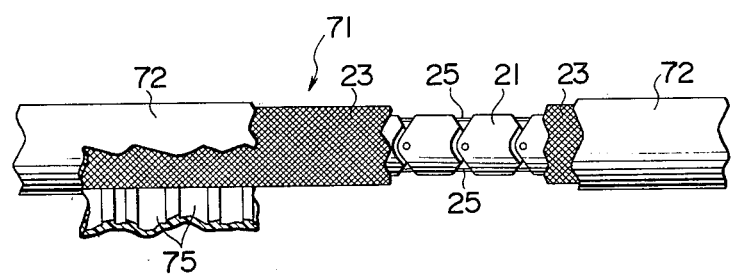
FIGS. 6(A) and (B) are a plan view, partly cut away, and an enlarged cross section respectively of a flexible tube for an endoscope according to a further embodiment of the invention.
Figure 6B:
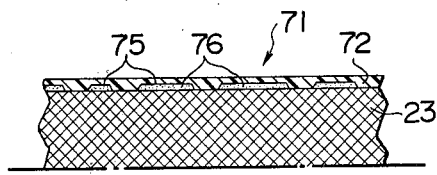

FIGS. 6(A) and (B) illustrate a further embodiment of the invention. A bendable portion 71, which again forms part of a flexible tube for endoscope, has a sheath tube 72, the internal peripheral surface of which is formed with a number of circumferentially extending grooves 75 of different widths so as to correspond to various positions assumed by the bendable portion 71 as it is flexed. In this manner, there is provided a change in the bending resistance. An anti-friction agent 76 is applied to and retained in these grooves 75, maintaining the smoothness of movement over a prolonged period of time. In addition, this arrangement greatly facilitates a flexing of the bendable portion 71 to a given position. While in the present embodiment, a number of circumferentially extending grooves 75 of different widths are formed so as to correspond to the positions assumed by the bendable portion 71 as it is flexed, the spacing between or depths of the grooves 75 may be changed to achieve a similar effect.

Figure 7:
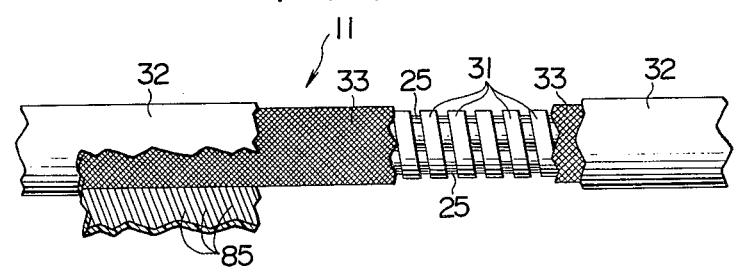
FIG. 7 is a plan view, partly cut away, of a flexible portion of a flexible tube for an endoscope according to still another embodiment of the invention.

The described embodiments are applied to a bendable portion which form part of the portion 3 which is adapted to be inserted into a coeliac cavity. FIG. 7 shows an embodiment in which the invention is applied to a flexible portion 11 which forms the majority of the portion 3. Specifically, the flexible portion 11 includes a sheath tube 32, the internal peripheral surface of which is formed with a number of narrow grooves 85 which retain an antifriction agent therein. The formation of the grooves 85 may be similar to those formed in the sheath tubes 42, 52, 62, 72 of the bendable portions 41, 51, 61, 71 or any other similarly functioning grooves. When the grooves 85 are formed in the inner peripheral surface of the sheath tube 32 to retain the antifriction agent therein, any reduction in the smoothness of movement can be avoided which might otherwise occur due to the antifriction agent being abraded off.

As discussed, in accordance with the invention, the antifriction agent is applied to and retained in grooves which are formed in the inner peripheral surface of the sheath tube, thereby allowing a flexible tube for endoscope to be provided which eliminates the disadvantages mentioned in the initial portion of the specification and which is very convenient in use.

In the embodiments shown in FIGS. 3 to 6, a bendable tube in the forms of bellows has been illustrated. However, it should be understood that the invention is equally applicable to a flexible tube having a bendable tube which is formed by a spiral coil, or a ribbon-shaped metal strip formed into a helical form.

In addition to the various configurations illustrated in the above embodiments, the grooves may be formed in a leash form, skewed line form, ring form or any other configuration desired.

What is claimed is:

1. A flexible tube for an endoscope, comprising:
    a control wire and an optical system extending along a longitudinal axis of said tube;
    a metallic braided sheath extending along said axis and surrounding said control wire and said optical system; and
    a sheath tube extending along said axis and surrounding said braided sheath such that an internal peripheral surface of said sheath tube is disposed in opposing relationship with said metallic braided sheath, said internal peripheral surface being formed with grooves which retain an anti-friction agent therein.

2. A flexible tube for an endoscope according to claim 1 in which said grooves have a width and a depth, at least one of the spacing between said grooves and the depth of said grooves varying locally so as to correspond to positions assumed by the flexible tube as it is flexed.

3. A flexible tube for an endoscope according to claim 1 wherein said flexible tube includes a bendable portion and wherein said grooves are formed in that portion of said internal peripheral surface of the sheath tube which covers said bendable portion of the flexible tube.

4. A flexible tube for an endoscope according to claim 1 wherein said grooves extend helically with respect to said longitudinal axis.

5. A flexible tube for an endoscope according to claim 1 in which said grooves are defined by fine meshes.

6. A flexible tube for an endoscope according to claim 1 in which said grooves are formed by a number of narrow grooves extending in said longitudinal direction.

7. A flexible tube for an endoscope according to claim 1 wherein said flexible tube includes a bendable portion, and wherein said grooves are formed in that portion of said internal peripheral surface of said sheath tube which covers said flexible portion of said flexible tube.

* * * * *